(12) United States Patent
Baars et al.

(10) Patent No.: US 6,703,243 B1
(45) Date of Patent: Mar. 9, 2004

(54) METHOD OF DETECTING PROTEIN AND A KIT USING THE SAME

(75) Inventors: Edwin Baars, Maarssen (NL); Guido Clemens Van den Brom, Maarssen (NL); Winfried Linxweiler, Darmstadt (DE)

(73) Assignee: JohnsonDiversey, Inc., Sturtevant, WI (US)

( * ) Notice: Subject to any disclaimer, the term of this patent is extended or adjusted under 35 U.S.C. 154(b) by 0 days.

(21) Appl. No.: 09/532,985

(22) Filed: Mar. 22, 2000

(30) Foreign Application Priority Data

Mar. 24, 1999 (EP) .............................. 99200917

(51) Int. Cl.$^7$ ............................ G01N 31/00; A61L 9/00; B08B 7/04
(52) U.S. Cl. ............................ 436/86; 422/28; 422/119; 134/18
(58) Field of Search ....................... 436/86, 55; 422/61, 422/58, 119, 28; 134/18

(56) References Cited

U.S. PATENT DOCUMENTS

| | | | | |
|---|---|---|---|---|
| 3,953,605 A | * | 4/1976 | Bauman | 424/54 |
| 4,013,416 A | | 3/1977 | Rittersdorf et al. | |
| 4,239,495 A | | 12/1980 | Gindler et al. | |
| 4,278,653 A | * | 7/1981 | Harris et al. | 424/1 |
| 4,874,789 A | * | 10/1989 | Smith et al. | 514/551 |
| 5,726,062 A | * | 3/1998 | Numa et al. | 436/86 |
| 5,998,358 A | * | 12/1999 | Herdt et al. | 510/197 |
| 6,218,349 B1 | * | 4/2001 | Kravitz et al. | 510/218 |

FOREIGN PATENT DOCUMENTS

| | | |
|---|---|---|
| EP | 0 545 128 A1 | 6/1993 |
| EP | 0 738 891 A2 | 4/1995 |
| EP | 0 785 429 A1 | 1/1996 |
| WO | 93/19152 | 9/1993 |

OTHER PUBLICATIONS

European Search Report dated Sep. 10, 1999.

* cited by examiner

*Primary Examiner*—Jill Warden
*Assistant Examiner*—Monique T. Cole
(74) *Attorney, Agent, or Firm*—Warren R. Bovee; Neil E. Hamilton; Renee J. Rymarz

(57) ABSTRACT

A method for detecting protein present on the surface of a sample is disclosed, wherein substances present on a portion of said surface are transferred to a sampling means and wherein, subsequently, these substances are contacted with a reagent capable of forming or changing color upon reaction with protein. Finally, the color changed or formed by this reaction is visually determined. In this method, the substances transferred onto the sampling means are also contacted with a specific type of nonionic or zwitterionic surfactant.

8 Claims, No Drawings

METHOD OF DETECTING PROTEIN AND A KIT USING THE SAME

FIELD OF THE INVENTION

The present invention relates to a method of detecting protein present on the surface of a sample wherein substances present on a portion of said surface are transferred to a sampling means and wherein, subsequently, these substances are contacted with a reagent capable of forming or changing colour upon reaction with protein. The invention also relates to a kit for detecting protein using this method.

BACKGROUND OF THE INVENTION

Soil (i.e. dirt or contamination) of mainly organic origin, and typically comprising protein, carbohydrate and/or fat, may be present on the surface of objects which come into contact with foodstuffs. This type of soil is generally associated with bacterial or microbial contamination which may present a risk to health. In order to visualize said soil it is convenient to use a reagent, such as certain dyes, which binds protein. By disclosing protein-containing soil, the location of the contamination can be indirectly visualised and can be targeted for effective cleaning. Consequently, methods for easily detecting protein have been developed in the past.

In most of the known methods for detection of protein, the surface of a sample is directly contacted by a reagent capable of forming colour upon reaction with protein. These known methods are less desirable because the colored material formed remains on the surface of the sample and can often hardly be removed with water.

As a result, the subject portion of the sample may be easily contaminated. Another problem associated with these known methods is that they generally require a long detection time.

In order to overcome these drawbacks, EP-A-738,891 (Konica) discloses a method to detect the presence of protein by transferring a substance to be detected from the surface of a sample to a water-absorbable portion of a sampling means (said portion comprising a water-insoluble synthetic polymer). This method solves the problem of contamination of the sample. Furthermore, the detection time for performing a good analysis could be expedited using this method. It is explicitly mentioned in this prior art document that the water-absorbable portion of the sampling means used in the method disclosed therein contains a synthetic polymer.

The method disclosed by EP-A-738,891 further includes the steps of contacting the transferred substances with a reagent capable of forming colour upon reaction with protein, and of measuring colour formed by this reaction so as to determine the presence of protein in the substance concerned.

When applying this method for hygiene monitoring, it has been found that it gives generally good results using any of the various protein detection methods described in EP-A-738,891. However, when this hygiene monitoring method was applied using the Coomassie protein detection dye method for monitoring the cleanliness of surfaces treated with quaternary ammonium compounds, it was found that residues of these compounds may negatively influence the detection method. Reason is that these compounds may react with the colour-forming reagent, resulting in a strong colour formation even in the absence of protein.

This effect is called false positive reading caused by the quaternary ammonium compounds.

Furthermore, the prior art contains various documents which refer to colourant containing compositions, test devices and methods for determining the presence or concentration of proteins, such as albumin, in body fluids, such as urine.

For instance, EP-A-545,128 discloses a method, wherein a composition containing a colourant, a buffer and a hydrophobic polymeric compound is applied for measuring the presence of protein in urine. It is mentioned in this document that the number of false positive readings due to the presence of quaternary ammonium compounds, such as peptides, amino acids and creatinine, is reduced when using this composition.

In addition, DE-A-25 10 633 discloses a method for detecting proteins in urine, wherein a composition including an octahalogenated sulphophthalein, as colourant, is applied. This composition further contains a water-immiscible polypropylene glycol in order to overcome interference with N-containing compounds present in the urine sample tested and to reduce false positive reactions. It is noted that the prior art documents relating to methods for determining the presence of protein in urine samples, do not disclose anything about the negative influence caused by disinfectant-type quaternary ammonium compounds on the detection method for determining the presence of protein on a previously cleaned surface.

In view of the foregoing, it is an object of the present invention to eliminate, or at least reduce, this negative effect resulting in false positive readings and caused by residues of the disinfectant-type quaternary ammonium compounds on the results of this detection method, as disclosed by EP-A-738,891 (Konica).

In this connection, these effective disinfectant-type (or antimicrobial) quaternary ammonium compounds may be generally defined to be quaternary ammonium compounds having the formula $(R_1)(R_2)(R_3)(R_4)N^+X^-$ wherein $R_1$, $R_2$, $R_3$, and $R_4$ are independently a $C_1$–$C_{24}$ aliphatic group, a $C_1$–$C_4$ hydroxyaliphatic group, benzyl, $C_1$–$C_{24}$ alkyl benzyl, or halo benzyl, and $X^-$ represents an anion capable of imparting water solubility or dispersibility to the compound such as chloride, bromide, iodide, sulphate, methylsulphate, and others.

We have surprisingly found that this object can be achieved when contacting the substances transferred onto the sampling means with a nonionic or zwitterionic surfactant as specified in claim 1.

We have also found that this detection method can be advantageously carried out when applying a sampling means having a water-absorbable portion comprising a water-insoluble polymer. This polymer can be a synthetic polymer or a non-synthetic polymer. Cellulose is preferably used as non-synthetic polymer.

DEFINITION OF THE INVENTION

Accordingly, in one aspect the present invention provides a method for detecting protein present on the surface of a sample comprising the steps of:

transferring substances present on a subject portion of said surface to a sampling means which comprises a water absorbable portion comprising a water-insoluble polymer;

contacting the substances transferred onto said sampling means with a reagent capable of forming or changing colour upon reaction with protein;

visually determining color formed by the reaction of said reagent with protein, wherein the substances transferred onto the sampling means are also contacted with a zwitterionic surfactant or a non-ionic surfactant selected from the group consisting of
  (i) condensates of aliphatic carboxylic acids having about 8 to about 18 carbon atoms in an aliphatic chain and incorporating from about 2 to about 50 ethylene oxide and/or propylene oxide and/or butylene units,
  (ii) condensates of aliphatic alcohols having from about 6 to about 24 carbon atoms and incorporating from about 2 to about 50 ethylene oxide and/or propylene oxide and/or butylene oxide units,
  (iii) condensates of alkyl phenols having about 6 to 12 carbon atoms and incorporating from about 2 to 25 moles of ethylene oxide and/or propylene and/or butylene oxide,
  (iv) polyoxyethylene derivatives of sorbitan mono-, di- and tri-fatty acid esters wherein the fatty acid component has between 12 and 24 carbon atoms and the polyethylene chains contain between about 4 and 30 ethylene oxide units,
  (v) polyoxyethylene-polyoxypropylene block copolymers having the formula:

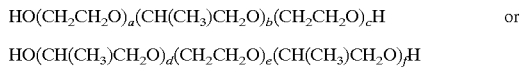

$HO(CH_2CH_2O)_a(CH(CH_3)CH_2O)_b(CH_2CH_2O)_cH$ or
$HO(CH(CH_3)CH_2O)_d(CH_2CH_2O)_e(CH(CH_3)CH_2O)_fH$ wherein a, b, c, d, e, and f are integers from 1 to 350 reflecting the respective polyethylene oxide and polypropylene oxide blocks of said polymer, wherein the polyoxyethylene component of the block polymer is at least about 10% of the block polymer,
  (vi) alkyl glycosides having formula:

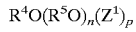

$R^4O(R^5O)_n(Z^1)_p$ wherein $R^4$ is a monovalent organic radical, for example a monovalent saturated aliphatic, unsaturated aliphatic or aromatic radical such as alkyl, hydroxyalkyl, alkenyl, hydroxyalkenyl, aryl, alkylaryl, hydroxyalkylaryl, arylalkyl, alkenylaryl, arylalkenyl and the like having from about 6 to about 30 carbon atoms, wherein $R^5$ is a divalent hydrocarbon radical containing from 2 to about 4 carbon atoms such as ethylene, propylene or butylene (most preferably the unit $(R^5O)_n$ represents repeating units of ethylene oxide, propylene oxide and/or random or block combinations thereof); n is an integer from 0 to about 12; $Z^1$ represents a moiety derived from a reducing saccharide containing 5 or 6 carbon atoms (most preferably a glucose unit); and p-is a number from 0.5 to about 10.

A zwitterionic surfactant suitable for use in the method of the present invention is a compound with a hydrophilic portion consisting of positively charged as well as negatively charged moieties and a hydrophobic uncharged aliphatic and/or aromatic component having about 6 to about 30 carbon atoms. This compound contains an equal number of positively and negatively charged moieties that give an overall uncharged or neutral compound having a pH-value in the range of about 1–9, more preferably 2–5.

Examples of negatively charged moieties are anionic groups such as sulphate, sulphonate, phosphate, or phosphonate. Examples of zwitterionic head groups are sulfobetaines, taurine, esters of phosphoric acid with choline or aminoethanol.

Suitable types of zwitterionic surfactant are 3-(3-Cholamidopropyl)-dimethylammonio-propanesulfonate (CHAPS) en (3-(3-Cholamidopropyl)dimethylammonio-2-hydroxy-1-propanesulfonate (CHAPSO).

In another aspect, the invention provides a kit for detecting protein including a combination of a sampling means comprising a water-absorbable portion (which comprises a water-insoluble polymer), for transferring substances present on a subject portion of the surface of a sample, a reagent capable of forming or changing colour upon reaction with protein, and a nonionic or zwitterionic surfactant according to claim 1. The polymer used in the present invention may be a synthetic polymer or a non-synthetic polymer, such as cellulose.

DETAILED DESCRIPTION OF THE INVENTION

The method according to the present invention is a method for qualitatively detecting protein on surfaces, particularly on those surfaces which have previously been treated with disinfectant-type quaternary ammonium compounds. When applying this method, it was found to be possible to mask (i.e. eliminate) the effect of up to 300 micrograms of any such quaternary ammonium compounds per sample.

On the other hand this type of quaternary ammonium compounds was found to give rise to a strong colour formation within 1 minute when no nonionic surfactant according to the present invention was present.

To avoid drying effects, best results are obtained when colour formation due to protein in the sample is monitored within 20 minutes after taking the sample concerned.

The method of the present invention is preferably carried out using the following procedure.

Substances which may contain protein are transferred from a portion of the surface of a sample to a sampling means. Subsequently, the sampling means is contacted with a previously prepared solution containing a nonionic or zwitterionic surfactant according to the present invention and the reagent capable of forming or changing colour upon reaction with protein, by adding said solution to the portion of the sampling means onto which the substances are transferred.

This solution, which is desirably an aqueous solution, is preferably added dropwise to the portion of the sampling means onto which substances are transferred.

Then the qualitative detection of protein is carried out by visually determining colour formed by the reaction of said reagent with protein.

Preferably, a nonionic surfactant selected from the group consisting of condensates of aliphatic alcohols having from about 6 to about 24 carbon atoms and incorporating from about 2 to 50 ethylene oxide units is used in the method of the invention. More preferably, the nonionic surfactant used in the invention is a condensate as mentioned above incorporating from 20 to 25 ethylene oxide units. Most preferably, this ethoxylate-type nonionic surfactant has an HLB-value in the range of 12–20.

When a solution containing the nonionic or zwitterionic surfactant and the reagent capable of forming colour is applied, the concentration of the nonionic surfactant in the aqueous solution is desirably in the range of 1–20%, more preferably 2–15%, by weight.

In the method of the invention, the sampling means comprises a water-insoluble (synthetic or non-synthetic) polymer to which protein containing substances present on the surface of a sample can be transferred. If this polymer is a non-synthetic polymer, it is may be cellulose, cellulose acetate or acetylated cellulose.

The sampling means for use in the method of the present invention can be of any shape as long as it has a portion having high water-absorbability.

Furthermore, it is preferable for convenience of sampling to attach a holding member to the water-absorbable portion comprising the non-synthetic polymer.

Examples of such desirable sampling means include the following:
- a swab-stick-shaped sampling means having the water-absorbable swab at the end of a stick;
- a tape-shaped sampling means which is composed of a water-absorbable portion located on a tape;
- a stamp-shaped sampling means in which a water-absorbable layer containing the non-synthetic polymer is attached on the stamping surface of a stamp-like handle;
- a filter paper-shaped sampling means containing the non-synthetic polymer made in the form of a filter paper; and
- a strip-shaped sampling means comprising a substrate, such as a plastic film, and a water-absorbable layer containing the non-synthetic polymer and located on the substrate, said sampling means cut in the form of a strip and having a space for handling.

By using any suitable sampling means out of the above list, the step of transferring substances from the surface of a sample to the sampling means, may be carried out by means of wiping, pressure contacting and absorbing. For the method of wiping, a sampling means in the form of a cotton swab connected to a stick or a membrane filter may be suitably applied. For the method of pressure contacting, a tape-shaped or stamp-shaped sampling means may be suitable applied. Furthermore, for the method of absorbing, a swab-stick shaped or a filter paper-shaped sampling means may be effectively applied for absorbing the substances to be transferred.

The sampling means used in the method of the present invention preferably has a water-absorbable portion which is wettable with an aqueous medium. More preferably, in the method of the invention the water-absorbable is made wet using an aqueous medium before substances from the sample surface are transferred thereto.

As an aqueous medium suitable for wetting the absorbable portion, an isotonic sodium chloride solution, purified water such as distilled water or deionized water, an aqueous solution containing an anionic surface active agent, an aqueous 2–95% solution of water-miscible organic solvent such as acetone, ethanol, propyl alcohol or methylethyl ketone can be mentioned.

The substances transferred to the sampling means from the sample surface are contacted with a reagent capable of forming colour upon reaction with protein for detecting the presence of protein in the transferred substances.

As the reagent for detecting protein, those necessary for detection according to the various protein detecting methods, such as biuret reaction method, Lowry method, Coomassie dying method, BCA method and ninhydrin reaction method, are usable in the method of the invention.

The reagent for detecting protein is preferably selected from the group of non-octahalogenated sulfophthaleines, desirably from the group consisting of phenol sulfonephthaleins and cresol sulfonephthaleins. Suitable reagents are for instance bromophenol blue, bromocresol green, bromocresol purple, bromophenol red, bromothymol blue, and bromochlorophenol. Very good results were obtained when using bromocresol green.

The reaction of the transferred substances with the reagent can be performed at ambient temperature.

The protein detection kit for applying the above-mentioned method of the invention, includes a sampling means according to the invention, a protein detecting reagent capable of reacting with protein and producing a colour, and a nonionic or zwitterionic surfactant according to the present invention and suitable for eliminating the above-described negative effect of quaternary ammonium compounds on the protein detection method. Desirably, the protein detection kit of the invention also includes a wetting solution.

The invention is further illustrated by the following non-limiting Examples, in which parts and percentages are by weight unless otherwise stated.

In the Examples the following abbreviations are used:
Dehydol TA20-Nonionic surfactant, C16–C18 ethoxylated alcohol containing on average 20 EO groups;
Lutensol AT25-Nonionic surfactant, C16–C18 ethoxylated alcohol containing on average 25 EO groups;
Tween 20-Nonionic surfactant, polyoxyethylene sorbitan monolaurate;
IPA-Isopropylalcohol
ADBAC-Quaternary ammonium compound, n-alkyl-dimethylbenzylammoniumchloride, wherein n is C12, C14, or C16 (Arquad)
BSA-Bovine serum albumin
BCG-Bromocresolgreen
CHAPS-(Cholamidopropyl)-dimethylammono-propanesulfonate (zwitterionic surfactant)

EXAMPLES A, 1–4

In these examples, the detection limit of various colourant containing solutions was determined with regard to the detection of ADBAC and BSA. The colourant present in these solutions was bromocresolgreen.

These solutions have following compositions:

| Example nr. | A % wt | 1 % wt | 2 % wt | 3 % wt | 4 % wt |
|---|---|---|---|---|---|
| Bromocresolgreen | 0.067 | 0.067 | 0.067 | 0.067 | 0.067 |
| Isopropylalcohol | 30.0 | 30.0 | 30.0 | 30.0 | 30.0 |
| Acetic acid | 3.2 | 3.2 | 3.2 | 3.2 | 3.2 |
| Citric acid | 0.2 | 0.2 | 0.2 | 0.2 | 0.2 |
| Ethyl acetate | 1.0 | 1.0 | 1.0 | 1.0 | 1.0 |
| Lutensol AT25 | — | 10.0 | — | — | — |
| Dehydol TA20 | — | — | 10.0 | — | — |
| Tween 20 | — | — | — | 10.0 | — |
| CHAPS | — | — | — | — | 10.0 |
| Water | 65.5 | 55.5 | 55.5 | 55.5 | 55.5 |

Two levels of the quaternary ammonium compound ADBAC were applied onto stainless steel plates having a surface area of 10 cm2. The ADBAC levels per stainless steel plate were: 100 $\mu$g and 200 $\mu$g.

The amount of ADBAC to be applied to the stainless steel plates was calculated assuming that, after applying an ADBAC containing solution, a residual water level of 1 mm remains on the surface of the stainless steel plate. Using this assumption it can be calculated that after drying 100 mg respectively 200 mg ADBAC per m2 will be present on a surface after applying a solution containing 100 ppm respectively 200 ppm ADBAC for disinfecting that surface. Since a surface of 10 cm2 is sampled in the present example, it can be derived that, when using a solution containing e.g. 200 ppm ADBAC, 200 μg ADBAC is taken up when sampling the surface of the stainless steel plate.

The surface of these plates was sampled by applying a plastic strip having a cellulose pad on top. Before sampling, the pad on the strip was wetted with a solution consisting of 30% IPA and 70% water.

After sampling, one of the above colourant containing solutions was added to the cellulose pad.

Colour was judged (i) immediately after adding the colourant containing solutions (i.e. at t=0 minutes), (ii) after 2 minutes, and (iii) after 5 minutes.

The colour development was judged using the following signs: −, +/−, +, ++, where − means orange, +/− means slight green, + means green, and ++ means dark green. In this connection, an orange colour means absence of protein, whereas a green colour is an indication for the presence of protein, when no false positive reaction takes place.

The colour development results are shown in Table 1.

TABLE 1

| ADBAC-level | 100 μg | | | 200 μg | | |
|---|---|---|---|---|---|---|
| Measuring time | t = 0 | t = 2 | t = 5 | t = 0 | t = 2 | t = 5 |
| Example A | − | ++ | ++ | − | ++ | ++ |
| Example 1 | − | − | − | − | − | − |
| Example 2 | − | − | − | − | − | − |
| Example 3 | − | − | − | − | − | − |
| Example 4 | − | − | − | − | − | − |

It can be noticed that Example A wherein a solution was applied not containing any surfactant shows a dark green colour development which means a strong false positive reaction caused by the presence of the ADBAC on the plates sampled. On the other hand, in Examples 1–4 wherein solutions were applied containing various nonionic or zwitterionic surfactants as shown above, no green colour development was found. In other words, no false positive reaction was detectable in Examples 1–4. It follows that addition of the indicated surfactants to the colourant containing solution was found to effectively inhibit false positive reactions in the presence of the quaternary ammonium compound ADBAC and in the absence of any proteins.

In the following experiments the suitability of the described nonionic and zwitterionic surfactants for detection of various amounts of proteins (BSA) on surfaces was investigated in the absence of ADBAC.

For this purpose, various levels of BSA were applied onto stainless steel plates having a surface area of 10 cm2. The BSA-levels applied per stainless steel plate were: 20 μg, 30 μg, and 50 μg.

Judgement of colour development was done using the same signs as applied in the above experiments (see Table 1). Also the meaning of the signs is the same: an orange colour means absence of protein, whereas a green colour is an indication for the presence of protein.

The colour development results are shown in Table 2.

TABLE 2

| BSA-level (μg) | 20 | | | 30 | | | 50 | | |
|---|---|---|---|---|---|---|---|---|---|
| Measuring time | t = 0 | t = 2 | t = 5 | t = 0 | t = 2 | t = 5 | t = 0 | t = 2 | t = 5 |
| Example A | +/− | + | + | + | + | + | + | ++ | ++ |
| Example 1 | +/− | + | +/− | +/− | + | + | + | ++ | ++ |
| Example 2 | +/− | + | +/− | +/− | + | + | + | ++ | ++ |
| Example 3 | +/− | +/− | +/− | +/− | + | + | + | ++ | ++ |
| Example 4 | +/− | +/− | +/− | +/− | + | + | + | ++ | ++ |

It can be noticed that the detection limit when using the solution of Examples 1–4 is not significantly different from that when applying the solution of comparative Example A not containing any nonionic or zwitterionic surfactant.

EXAMPLE 5

In this example, experiments are described wherein the presence of BSA was tested in combination with the quaternary ammonium compound ADBAC.

First, a predetermined amount of BSA was added onto a stainless steel plate (having a surface area of 10 cm2) and after drying ADBAC was added to said plate.

The amount of ADBAC to be applied to the stainless steel plates tested was calculated using the same assumptions as applied in the above-described experiments.

The surface of 10 cm2 stainless steel plates onto which various amounts of BSA and ADBAC were applied, was sampled using the colourant containing solutions of Examples 1–4. Also the sampling method and the judging method for estimating the colour development were equal to those of Examples 1–4. The colour development was judged immediately after addition of the colourant containing solution, after 2 minutes, and after 5 minutes.

The results for BSA-levels of 50 μg, 100 μg and 150 μg are shown respectively in Tables 3, 4, and 5.

TABLE 3

| ADBAC-level (in μg) | 100 | | | 200 | | | 300 | | |
|---|---|---|---|---|---|---|---|---|---|
| measuring time | t = 0 | t = 2 | t = 5 | t = 0 | t = 2 | t = 5 | t = 0 | t = 2 | t = 5 |
| solution of Example 1 | − | +/− | + | − | +/− | +/− | − | − | +/− |
| solution of Example 2 | − | +/− | + | − | +/− | +/− | − | − | +/− |
| solution of Example 3 | − | +/− | + | − | +/− | +/− | − | − | +/− |
| solution of Example 4 | − | +/− | + | − | +/− | +/− | − | − | +/− |

TABLE 4

| ADBAC-level (in μg) | 100 | | | 200 | | | 300 | | |
|---|---|---|---|---|---|---|---|---|---|
| measuring time | t = 0 | t = 2 | t = 5 | t = 0 | t = 2 | t = 5 | t = 0 | t = 2 | t = 5 |
| solution of Example 1 | +/− | + | ++ | +/− | + | ++ | − | +/− | + |
| solution of Example 2 | +/− | + | + | − | +/− | + | − | − | +/− |

TABLE 4-continued

| ADBAC- | 100 | | | 200 | | | 300 | | |
|---|---|---|---|---|---|---|---|---|---|
| level (in µg) measuring time | t = 0 | t = 2 | t = 5 | t = 0 | t = 2 | t = 5 | t = 0 | t = 2 | t = 5 |
| solution of Example 3 | +/− | + | + | +/− | + | ++ | +/− | +/− | + |
| solution of Example 4 | +/− | + | + | +/− | + | ++ | +/− | +/− | + |

TABLE 5

| ADBAC- | 100 | | | 200 | | | 300 | | |
|---|---|---|---|---|---|---|---|---|---|
| level (in µg) measuring time | t = 0 | t = 2 | t = 5 | t = 0 | t = 2 | t = 5 | t = 0 | t = 2 | t = 5 |
| solution of Example 1 | + | + | ++ | + | + | ++ | +/− | +/− | + |
| solution of Example 2 | + | + | ++ | + | + | ++ | +/− | +/− | + |
| solution of Example 3 | + | + | ++ | + | + | ++ | +/− | +/− | + |
| solution of Example 4 | + | + | ++ | + | + | ++ | +/− | +/− | + |

From the results shown in tables 3–5, it can be derived that using the colourant containing solutions of examples 1–4 the protein bsa can be detected in the presence of quaternary ammonium compounds after at least 2 minutes.

What is claimed is:

1. A method for detecting protein present on the surface of a sample, the method comprising the steps of:
   treating the surface or the sample with a disinfectant or antimicrobial agent, the disinfectant or antimicrobial agent being a quaternary ammonium compound;
   transferring substances present on a subject portion of said surface to a sampling means which comprises a water absorbable portion comprising a water-insoluble polymer;
   contacting the substances transferred onto said sampling means with a reagent which is a non-halogenated compound selected from the group consisting of phenolsulphonephthaleins and cresolsulphonephonephthaleins capable of forming or changing color upon reaction with protein;
   visually determining color changed or formed by the reaction of said reagent with protein,
   wherein the substances transferred onto the sampling means are also contacted with a nonionic surfactant selected from the group consisting of
   (i) condensates of aliphatic carboxylic acids having about 8 to about 18 carbon atoms in an aliphatic chain and incorporating from about 2 to about 50 ethylene oxide and/or propylene oxide and/or butylene units,
   (ii) condensates of aliphatic alcohols having from about 6 to about 24 carbon atoms and incorporating from about 2 to about 50 ethylene oxide and/or propylene oxide and/or butylene oxide units,
   (iii) condensates of alkyl phenols having about 6 to 12 carbon atoms and incorporating from about 2 to 25 moles of ethylene oxide and/or propylene and/or butylene oxide,
   (iv) polyoxyethylene derivatives of sorbitan mono-, di- and tri-fatty acid esters wherein the fatty acid component has between 12 and 24 carbon atoms and the polyethylene chains contain between about 4 and 30 ethylene oxide units,
   (v) polyoxyethylene-polyoxypropylene block copolymers having the formula:

$HO(CH_2CH_2O)_a(CH(CH_3)CH_2O)_b(CH_2CH_2O)_cH$ or $HO(CH(CH_3)CH_2O)(CH_2CH_2O)_e(CH(CH_3)CH_2O)_fH$ wherein a, b, c, d, e, and f are integers from 1 to 350 reflecting the respective polyethylene oxide blocks of said polymer, wherein the polyoxyethylene component of the block polymer is at least about 10% of the block polymer,
   (vi) alkyl glycosides having formula:

$R^4O(R^5O)_n(Z^1)_p$ wherein $R^4$ is a monovalent organic radical, for example a monovalent saturated aliphatic, unsaturated aliphatic or aromatic radically such as alkyl, hydroxyalkyl, alkenyl, hydroxyalkenyl, aryl, alkylaryl, hydroxyalkylaryl, arylalkyl, alkenylaryl, arylalkenyl and the like having from about 6 to about 30 carbon atoms, wherein $R^5$ is a divalent hydrocarbon radical containing from 2 to about 4 carbon atoms such as ethylene, propylene or butylene (most preferably the unit $(R^5O)_n$ represents repeating units of ethylene oxide, propylene oxide and/or random or block combinations thereof); N is an integer from 0 to about 12; $Z^1$ represents a moiety derived from a reducing saccharide containing 5 or 6 carbon atoms; and p is a number from 0.5 to about 10, or a zwitterionic surfactant, or mixtures of these surfactants.

2. Method according to claim 1, wherein the nonionic surfactant is selected from the group consisting of condensates of aliphatic alcohols including from 6 to 24 carbon atoms, incorporating from 20 to 25 moles of ethylene oxide and having an HLB-value in the range from 12–20.

3. The method according to claim 1, wherein the nonionic or zwitterionic surfactant and the reagent capable of forming colour upon reaction with protein are contained in a solution, and wherein the steps of contacting said reagent and said nonionic or zwitterionic surfactant with the substances transferred to the sampling means are carried out by adding said solution to the portion of the sampling means on to which the substances are transferred.

4. The method according to claim 3, wherein the solution containing the nonionic or zwitterionic surfactant and the reagent is added dropwise to the portion of the sampling means onto which the substances are transferred.

5. The method according to claim 3, wherein the solution contains from 1 to 20% wt, preferably from 2 to 15% wt, of the nonionic or zwitterionic surfactant.

6. The method claim 5, wherein the water-absorbable portion of the sampling means is wetted with a wetting fluid in advance of the transferring step.

7. A kit for detecting protein including a combination of a sampling means comprising a water-absorbable portion which comprises a water-insoluble polymer, for transferring substances present on the subject portion of the surface of a sample, a reagent capable of forming or changing color upon reaction with protein, and a nonionic or zwitterionic surfactat or mixtures thereof wherein said nonionic surfactant is selected from the group consisting of
   (i) condensates of aliphatic carboxylic acids having about 8 to about 18 carbon atoms in an aliphatic chain and incorporating from about 2 to about 50 ethylene oxide and/or propylene oxide and/or butylene units,
   (ii) condensates of aliphatic alcohols having from about 6 to about 24 carbon atoms and incorporating from about 2 to about 50 ethylene oxide and/or propylene oxide and/or butylene oxide units, (iii) condensates of alkyl phenols having about 6 to 12 carbon atoms and incorporating from about 2 to 25 moles of ethylene oxide and/or propylene and/or butylene oxide, (iv) polyoxyethylene derivatives of sorbitan mono-, di- and tri-fatty acid esters wherein the fatty acid component has between 12 and 24 carbon atoms and the polyethylene chains contain between about 4 and 30 ethylene oxide units, (v) polyoxyethylene-polyoxypropylene block copolymers having the formula:

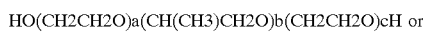

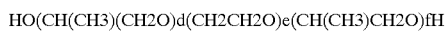

wherein a, b, c, d, e, and f are integers from 1 to 350 reflecting the respective polyethylene oxide and polypropylene oxide blocks of said polymer, wherein the polyoxyethylene component of the block polymer is at least about 10% of the block polymer, (vi) alkzyl glycosides having formula:

R4O(R5O)n(Z1)p wherein R4 is a monovalent organic radical, for example a monovalent saturated aliphatic, unsaturated aliphatic or aromatic radical such as alkyl, hydroxyalkyl, alkenyl, hydroxyalkenyl, aryl, alkylaryl, lydroxyalkylaryl, arylalkyl, alkenylaryl, arylalkenyl and the like having from about 6 to about 30 carbon atoms, wherein R5 is a divalent hydrocarbon radical containing from 2 to about 4 carbon atoms such as ethylene, propylene or butylenes (most preferably the unit (R5O)n represents repeating units of ethylene oxide, propylene oxide and/or random or block combinations thereof); n is an integer from 0 to about 12; Z1 represents a moiety derived from a reducing saccharide containing 5 or 6 carbon atoms; and p is a number from 0.5 to about 10, and wherein the kit further comprises a disinfectant, an antimicrobial agent, or both.

8. The kit according to claim 7, wherein the reagent and the nonionic or zwitterionic surfactant are components of a solution.

* * * * *